(12) United States Patent
Sugawara et al.

(10) Patent No.: US 10,564,134 B2
(45) Date of Patent: Feb. 18, 2020

(54) PSEUDO DEFECT SAMPLE, PROCESS FOR PRODUCING THE SAME, METHOD FOR ADJUSTING ULTRASONIC FLAW DETECTION MEASUREMENT CONDITION, METHOD FOR INSPECTING TARGET MATERIAL, AND PROCESS FOR PRODUCING SPUTTERING TARGET

(71) Applicant: SUMITOMO CHEMICAL COMPANY, LIMITED, Tokyo (JP)

(72) Inventors: Hiroaki Sugawara, Niihama (JP); Koji Nishioka, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/771,205

(22) PCT Filed: Jan. 18, 2018

(86) PCT No.: PCT/JP2018/001351
§ 371 (c)(1),
(2) Date: Mar. 8, 2019

(87) PCT Pub. No.: WO2018/139330
PCT Pub. Date: Aug. 2, 2018

(65) Prior Publication Data
US 2019/0265201 A1  Aug. 29, 2019

(30) Foreign Application Priority Data

Jan. 24, 2017 (JP) ................................. 2017-010579
Jul. 28, 2017 (JP) ................................. 2017-146696

(51) Int. Cl.
*G01N 29/30* (2006.01)
*G01N 29/04* (2006.01)
*G01N 29/44* (2006.01)

(52) U.S. Cl.
CPC .......... *G01N 29/30* (2013.01); *G01N 29/043* (2013.01); *G01N 29/4418* (2013.01)

(58) Field of Classification Search
CPC .. G01N 29/30; G01N 29/043; G01N 29/4418; G01N 2291/0235;
(Continued)

(56) References Cited

U.S. PATENT DOCUMENTS 4,331,021 A * 5/1982 Lopez ................... A61B 8/587
  73/1.86
5,887,481 A * 3/1999 Leroy ................. C23C 14/3414
  73/866

(Continued)

FOREIGN PATENT DOCUMENTS

CN  103235045 A  8/2013
CN  104777237 A  7/2015
(Continued)

OTHER PUBLICATIONS

Decision to Grant a Patent (including an English translation thereof) issued in the Japanese Patent Application No. 2017-146696 dated Dec. 5, 2017.
(Continued)

*Primary Examiner* — Lisa M Caputo
*Assistant Examiner* — Rose M Miller
(74) *Attorney, Agent, or Firm* — Birch, Stewart, Kolasch & Birch, LLP (57) ABSTRACT

A pseudo defect sample for adjusting an ultrasonic flaw detection measurement condition to inspect a defect within a target material,
  the pseudo defect sample comprising a substrate which has a first surface and a second surface opposed to the first surface,
  the substrate having a counterbore which is formed therein from a side of the first surface to a first depth,
(Continued)

and a flat-bottomed hole which is formed from the bottom surface of the counterbore to a second depth and formed in a part of a bottom surface of the counterbore, and a ratio $\phi/d$ of an equivalent circle diameter $\phi$ of the flat-bottomed hole to the second depth d of the flat-bottomed hole being:

0.08 or more and less than 0.40 when the equivalent circle diameter $\phi$ of the flat-bottomed hole is less than 0.3 mm;

0.1 or more and less than 0.60 when the equivalent circle diameter $\phi$ of the flat-bottomed hole is 0.3 mm or more and less than 0.4 mm; and 0.11 or more and less than 1.60 when the equivalent circle diameter $\phi$ of the flat-bottomed hole is 0.4 mm or more.

13 Claims, 6 Drawing Sheets

(58) Field of Classification Search
CPC ... G01N 2291/0234; G01N 2291/0289; G01N 2291/2691
USPC .......................................................... 73/1.86
See application file for complete search history.

(56) References Cited

U.S. PATENT DOCUMENTS

| 6,415,644 | B1* | 7/2002 | Rockwood | G01B 17/02 |
| | | | | 73/1.86 |
| 6,439,054 | B1 | 8/2002 | Gore et al. | |
| 7,617,715 | B2* | 11/2009 | Georgeson | G01N 29/11 |
| | | | | 29/593 |
| 8,181,523 | B2 | 5/2012 | Batzinger et al. | |
| 2007/0028661 | A1 | 2/2007 | Girshovich et al. | |
| 2010/0018311 | A1 | 1/2010 | Batzinger et al. | |

FOREIGN PATENT DOCUMENTS

| JP | 56-107156 A | 8/1981 |
| JP | 61-96461 A | 5/1986 |
| JP | 7-27751 A | 1/1995 |
| JP | 2001-40471 A | 2/2001 |
| JP | 2010-145401 A | 7/2010 |
| JP | 2017-207345 A | 11/2017 |

OTHER PUBLICATIONS

Notification of Reasons for Refusal (including an English translation thereof) issued in the Japanese Patent Application No. 2017-146696 dated Sep. 12, 2017.
Written Opinion of the International Searching Authority (including an English translation thereof) issued in the corresponding International Application No. PCT/JP2018/001351 dated Apr. 3, 2018.
An English translation of JP 7-27751 A, published on Jan. 31, 1995.
An English translation of the Written Opinion of the International Searching Authority issued in the corresponding International Application No. PCT/JP2018/001351 dated Apr. 3, 2018.
Chinese Notification of the First Office Action (including an English translation thereof) issued in the corresponding Chinese Patent Application No. 201880000346.8 dated Dec. 5, 2018.
International Search Report issued in the corresponding International Application No. PCT/JP2018/001351 dated Apr. 3, 2018.
Korean Written Opinion (including an English translation thereof) issued in the corresponding Korean Patent Application No. 10-2018-7012199 dated Oct. 5, 2018.
Zhang et al., "Design of Raw Materials Ultrasound Briquette by ASME Standard," Non-Destructive Testing, vol. 39, No. 5, Oct. 2015, pp. 23-29 (8 pages total; including one page of an English abstract).

* cited by examiner

|  |  | Second depth d of flat-bottomed hole d [mm] | | | | | | | | | | |
|---|---|---|---|---|---|---|---|---|---|---|---|---|
|  |  | 0.25 | 0.50 | 0.75 | 1.00 | 1.25 | 1.50 | 2.00 | 2.50 | 3.00 | 3.50 | 4.00 |
| Equivalent circle diameter of flat-bottomed hole φ [mm] | 0.2 | X | X | O | O | O | O | O | O | X | X | X |
|  | 0.25 | X | X | O | O | O | O | O | O | O | X | X |
|  | 0.3 | X | X | O | O | O | O | O | O | O | X | X |
|  | 0.4 | X | O | O | O | O | O | O | O | O | O | X |

FIG. 12

|  |  | Second depth d of flat-bottomed hole d [mm] | | | | | | | | | | |
|---|---|---|---|---|---|---|---|---|---|---|---|---|
|  |  | 0.25 | 0.50 | 0.75 | 1.00 | 1.25 | 1.50 | 2.00 | 2.50 | 3.00 | 3.50 | 4.00 |
| Equivalent circle diameter of flat-bottomed hole φ [mm] | 0.2 | 0.80 | 0.40 | 0.27 | 0.20 | 0.16 | 0.13 | 0.10 | 0.08 | 0.07 | 0.06 | 0.05 |
|  | 0.25 | 1.00 | 0.50 | 0.33 | 0.25 | 0.20 | 0.17 | 0.13 | 0.10 | 0.08 | 0.07 | 0.06 |
|  | 0.3 | 1.20 | 0.60 | 0.40 | 0.30 | 0.24 | 0.20 | 0.15 | 0.12 | 0.10 | 0.09 | 0.08 |
|  | 0.4 | 1.60 | 0.80 | 0.53 | 0.40 | 0.32 | 0.27 | 0.20 | 0.16 | 0.13 | 0.11 | 0.10 |

PSEUDO DEFECT SAMPLE, PROCESS FOR PRODUCING THE SAME, METHOD FOR ADJUSTING ULTRASONIC FLAW DETECTION MEASUREMENT CONDITION, METHOD FOR INSPECTING TARGET MATERIAL, AND PROCESS FOR PRODUCING SPUTTERING TARGET

TECHNICAL FIELD

The present invention relates to a pseudo defect sample for adjusting an ultrasonic flaw detection measurement condition to inspect defects within a target material, a process for producing the same, a method for adjusting an ultrasonic flaw detection condition, a method for inspecting a target material, and a process for producing a sputtering target.

BACKGROUND ART

Sputtering targets are utilized in sputtering widely used in the fields of manufacturing semiconductors and flat panel displays, and the like. When sputtering the sputtering target, if the target material has therein defects, such as holes, oxides, and foreign matter, abnormal discharge may occur due to these defects. This abnormal discharge may cause a phenomenon called "splash". The splash is a phenomenon in which a part of the target material melts, adheres to a substrate, and solidifies, and this phenomenon may cause a short circuit between wirings or electrodes with films deposited by sputtering.

To suppress abnormal discharge of the target material, target materials not containing any fine defects (e.g., 0.2 mm or more) are required. For this reason, when manufacturing the target material, it is necessary to inspect the present or absence of any defect within the target material. As the inspection method, there is a method for observing the change in reflected echo in ultrasonic waves using an ultrasonic probe.

To improve the measurement accuracy in inspection using the ultrasonic probe, the focus of the ultrasonic waves emitted from the ultrasonic probe is adjusted. A pseudo defect sample is used to adjust the focus of the ultrasonic waves emitted from the ultrasonic probe. The pseudo defect sample is provided with a hole having the same size as a fine defect in the target material. Then, the ultrasonic waves emitted from the ultrasonic flaw probe are focused on the hole, and then the reflected echo from the bottom surface of the hole is measured to adjust the sensitivity of the ultrasonic flaw detection.

JP 2010-145401 A describes pseudo defect samples. The pseudo defect sample has a counterbore and a flat-bottomed hole disposed at the bottom surface of the counterbore and having a diameter smaller than the diameter of the counterbore. The sensitivity of the ultrasonic flaw detection is adjusted by measuring the reflected echo from the bottom surface of the counterbore and the reflected echo from the bottom surface of the flat-bottomed hole.

The conventional pseudo defect sample is used to inspect defects of large-sized industrial parts. For this reason, the diameter of the flat-bottomed hole in the pseudo defect sample is set large. Hence, the ultrasonic waves emitted from the ultrasonic probe are easily focused directly on the smaller flat-bottomed hole.

However, since the conventional pseudo defect sample is not used for inspecting fine defects in the target material, in order to apply the pseudo defect sample to the target material as it is, the diameter of the flat-bottomed hole must be reduced.

PRIOR ART DOCUMENT

Patent Document

Patent Document 1: JP 2010-145401 A

DISCLOSURE OF THE INVENTION

Problems to be Solved by the Invention

It is an object of the present invention to provide a pseudo defect sample suitable for use in adjustment of an ultrasonic flaw detection measurement condition in an inspection method of a target material, a process for producing the same, a method for inspecting a target material, and a process for producing a sputtering target.

The pseudo defect sample of the present invention is a pseudo defect sample for adjusting an ultrasonic flaw detection measurement condition to inspect a defect within a target material, the pseudo defect sample comprising a substrate which has a first surface and a second surface opposed to the first surface, the substrate having a counterbore which is formed therein from a side of the first surface to a first depth, and a flat-bottomed hole which is formed in a part of a bottom surface of the counterbore and formed from the bottom surface of the counterbore to a second depth, and a ratio φ/d of an equivalent circle diameter φ of the flat-bottomed hole to the second depth d of the flat-bottomed hole being:

0.08 or more and less than 0.40 when the equivalent circle diameter φ of the flat-bottomed hole is less than 0.3 mm;

0.1 or more and less than 0.60 when the equivalent circle diameter φ of the flat-bottomed hole is 0.3 mm or more and less than 0.4 mm; and 0.11 or more and less than 1.60 when the equivalent circle diameter φ of the flat-bottomed hole is 0.4 mm or more.

Here, the term equivalent circle diameter of the flat-bottomed hole refers to the diameter of a circle when the flat-bottomed hole is circle, and also refers the diameter of a circle having an area equal to the area of the flat-bottomed hole when the flat-bottomed hole is not circular. Specifically, assuming that S is the area of the flat-bottomed hole, the equivalent circle diameter φ is $(4S/\pi)^{1/2}$.

According to the pseudo defect sample of the present invention, when the sensitivity adjustment of the ultrasonic flaw detection is performed in the adjustment of the ultrasonic flaw detection measurement condition using the pseudo defect sample, the reflected echo from the flat-bottomed hole can be recognized even if the ultrasonic waves emitted from the ultrasonic probe are focused on the bottom surface of the counterbore.

That is, the ultrasonic waves emitted from the ultrasonic probe can be focused on the bottom surface of the larger counterbore which is easy to detect, so that the smaller flat-bottomed hole can be recognized in such a state. Because of this, the ultrasonic probe can be easily positioned with respect to the flat-bottomed hole, which can simplify a work for focusing the ultrasonic waves emitted from the ultrasonic probe on the bottom surface of the flat-bottomed hole.

Therefore, according to the pseudo defect sample of the present invention, the sensitivity adjustment of the ultrasonic flaw detection becomes easy, so that the time required for the adjustment of the ultrasonic flaw detection measurement condition can be shortened.

The pseudo defect sample according to one embodiment of the invention, the equivalent circle diameter φ of the flat-bottomed hole is 0.5 mm or less.

In the embodiment of the pseudo defect sample, since the equivalent circle diameter φ is 0.5 mm or less, the flat-bottomed hole is small, which makes it difficult to focus the ultrasonic waves emitted from the ultrasonic probe directly on the flat-bottomed hole. In the present embodiment, such a flat-bottomed hole that is difficult to recognize can be easily recognized.

In an embodiment of the pseudo defect sample, the equivalent circle diameter φ of the flat-bottomed hole is 0.1 mm or more and less than 0.3 mm.

According to the present embodiment, since the equivalent circle diameter φ of the flat-bottomed hole is 0.1 mm or more and less than 0.3 mm, the flat-bottomed hole can be easily recognized in the present embodiment, even though the flat-bottomed hole is very small.

In an embodiment of the pseudo defect sample, the ultrasonic flaw detection measurement condition is a condition for performing ultrasonic flaw detection measurement with ultrasonic waves having a frequency of 5 MHz or more.

In an embodiment of the pseudo defect sample, the pseudo defect sample comprises a plurality of sets of the counterbores and the flat-bottomed holes.

According to the embodiment, the plurality of sets of the counterbores and the flat-bottomed holes are preferably provided.

By disposing the plurality of sets of flat-bottomed holes at the certain position located at the same depth as each other in the pseudo defect sample, the ultrasonic waves emitted from the ultrasonic probe can be focused to repeatedly perform the sensitivity adjustment of the ultrasonic flaw detection, to thereby improve the accuracy of the sensitivity adjustment. Furthermore, the plurality of flat-bottomed holes may have the same equivalent circle diameter or different equivalent circle diameters each other.

In one embodiment of the pseudo defect sample, the substrate is formed of aluminum, copper, titanium, silver, or an alloy containing at least one of these metal elements.

According to the present embodiment, these materials that configure the substrate are more likely to generate holes (defects) during production (melting and casting) of the target material. Therefore, when such a target material composed of any of these materials is used to produce a sputtering target, the ultrasonic flaw inspection is required to check the presence or absence of a defect. Accordingly, these materials are suitable for use in the pseudo defect sample.

A process for producing a pseudo defect sample, the pseudo defect sample being to adjust an ultrasonic flaw detection measurement condition for inspecting a defect within a target material, comprises the steps of:

forming a counterbore in a substrate which has a first surface and a second surface opposed to the first surface, from a side of the first surface to a first depth; and forming a flat-bottomed hole from the bottom surface to a second depth in a part of a bottom surface of the counterbore, a ratio φ/d of an equivalent circle diameter φ of the flat-bottomed hole to the second depth d of the flat-bottomed hole being: 0.08 or more and less than 0.40 when the equivalent circle diameter φ of the flat-bottomed hole is less than 0.3 mm; 0.1 or more and less than 0.60 when the equivalent circle diameter φ of the flat-bottomed hole is 0.3 mm or more and less than 0.4 mm; and 0.11 or more and less than 1.60 when the equivalent circle diameter φ of the flat-bottomed hole is 0.4 mm or more.

When the pseudo defect sample obtained from the above-mentioned manufacturing method is used to adjust the ultrasonic flaw detection measurement condition, the sensitivity adjustment of the ultrasonic flaw detection becomes easy, so that the time required for the adjustment of the ultrasonic flaw detection measurement condition can be shortened.

In an embodiment of the process for producing a pseudo defect sample, the substrate is formed of aluminum, copper, titanium, silver, or an alloy containing at least one of these metal elements.

According to the present embodiment, any of these materials that configure the substrate is more likely to generate holes (defects) during production (melting and casting) of the target material. Therefore, when such a target material composed of any of these materials is used to produce a sputtering target, the ultrasonic flaw inspection is required to check the presence or absence of a defect.

A method for adjusting an ultrasonic flaw detection measurement condition, comprises the steps of:

transmitting ultrasonic waves from an ultrasonic probe in such a manner that the waves move from a second surface of the substrate in the above-mentioned pseudo defect sample to the first surface of the substrate, followed by confirming a reflected echo of the counterbore;

focusing the ultrasonic waves on a bottom surface of the counterbore based on the reflected echo of the counterbore in the pseudo defect sample;

receiving a reflected echo that is reflected from the bottom surface of the flat-bottomed hole in the pseudo defect sample, while receiving a reflected echo that is reflected from the bottom surface of the counterbore; and focusing the ultrasonic waves on the bottom surface of the flat-bottomed hole based on the reflected echo from the bottom surface of the flat-bottomed hole.

According to the adjustment method mentioned above, when the sensitivity adjustment of the ultrasonic flaw detection is performed in the adjustment of the ultrasonic flaw detection measurement condition using the pseudo defect sample, the reflected echo from the bottom surface of the flat-bottomed hole can be recognized while being distinguished from the reflected echo of the bottom surface of the counterbore, even if the ultrasonic waves emitted from the ultrasonic probe are focused on the bottom surface of the counterbore.

That is, the ultrasonic waves emitted from the ultrasonic probe can be focused on the bottom surface of the larger counterbore which is easy to detect, so that the smaller flat-bottomed hole can be recognized in such a state. Owing to this, the ultrasonic probe can be easily positioned with respect to the flat-bottomed hole, which can simplify a work for focusing the ultrasonic waves emitted from the ultrasonic probe on the bottom surface of the flat-bottomed hole.

Therefore, the above-mentioned adjustment method can make the sensitivity adjustment of the ultrasonic flaw detection easy, so that the time required for the adjustment of the ultrasonic flaw detection measurement condition can be shortened.

In an embodiment of the adjustment method, the ultrasonic flaw detection measurement condition is a condition for performing ultrasonic flaw detection measurement with ultrasonic waves having a frequency of 5 MHz or more.

A method for inspecting a target material, comprises the steps of:

transmitting ultrasonic waves to a target material while scanning the target material by using an ultrasonic probe under the ultrasonic flaw detection measurement condition adjusted by the above-mentioned adjustment method;

measuring a reflected echo that is reflected from the target material; and determining a defect within the target material based on a result of the measurement.

According to the above-mentioned inspection method, by using the high-accuracy ultrasonic flaw detection measurement method, the quality of the target material can be determined satisfactorily.

An embodiment of the process for producing a sputtering target comprises the steps of: determining presence of a defect within the target material by the inspection method mentioned above; and machining the target material that is determined not to have substantially any defect therein.

Another embodiment of the process for producing a sputtering target comprises the steps of:

determining presence of a defect within the target material by the inspection method mentioned above; and joining the target material that is determined not to have substantially any defect therein, to a support member.

According to the above-mentioned process for producing the sputtering target, the use of the target material of good quality can improve the quality of the sputtering target.

Effects of the Invention

According to the pseudo defect sample and the production process of the present invention, the measurement conditions for the ultrasonic flaw detection can be easily set.

According to the method for adjusting an ultrasonic flaw detection measurement condition of the present invention, the sensitivity adjustment of the ultrasonic flaw detection can be easily performed. According to the method for inspecting a target material of the present invention, the quality of the target material can be easily determined. According to the process for producing the sputtering target of the present invention can produce the sputtering target of good quality.

BRIEF DESCRIPTION OF THE DRAWINGS

In FIG. 11, the region denoted by the circle sign as "0" is highlighted.

FIG. 12 It shows the relationship among the equivalent circle diameter $\phi$, the second depth d, and the ratio $\phi/d$. In FIG. 12, the area of "0" that is denoted in FIG. 11 is highlighted.

MODE FOR CARRYING OUT THE INVENTION

Embodiments of the present invention shown in the figures will be described in detail.

First Embodiment

Figure 1:
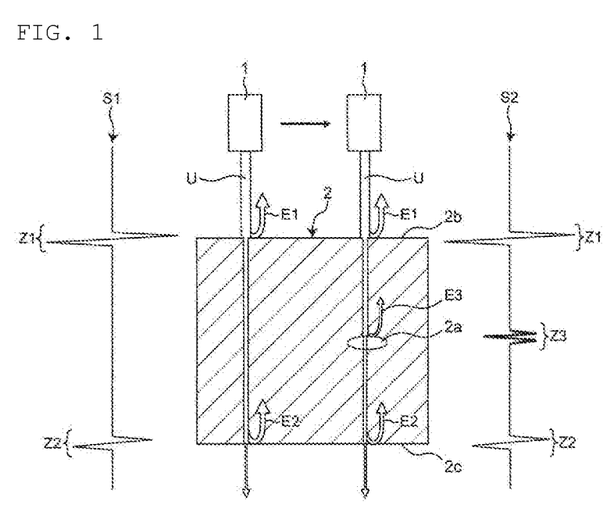
FIG. 1 It is an explanatory diagram for explaining the principle of ultrasonic flaw detection measurement used in the present invention.

FIG. 1 is an explanatory diagram for explaining the principle of ultrasonic flaw detection measurement used in the present invention. As shown in FIG. 1, an ultrasonic probe 1 is used for ultrasonic flaw inspection (UT: Ultrasonic Testing), which is a type of non-destructive inspection.

The ultrasonic flaw inspection will be described below. The ultrasonic pulse generated from a pulse transmitter is transmitted from the ultrasonic probe 1, and part of the ultrasonic pulse is reflected by the surface of a defect 2a inside an object to be inspected 2. The reflected wave is received by the ultrasonic probe 1 and converted into a high-frequency voltage. The converted signal is displayed on a display via a receiver, and the position and the level of the size of the defect 2a can be confirmed. In FIG. 1, the defect 2a indicates a hole.

Specifically, the ultrasonic probe 1 is moved from the left to the right in FIG. 1 along a surface 2b of the object to be inspected 2 while emitting ultrasonic waves U from the ultrasonic probe 1. As shown on the left side of FIG. 1, in a case where there is no defect within the object to be inspected 2, when ultrasonic waves U are emitted from the ultrasonic probe 1, a first reflected echo E1 is received from the surface 2b of the object to be inspected 2, and a second reflected echo E2 is received from a back surface 2c of the object to be inspected 2. At this step, a measurement signal S1 includes a first signal Z1 from the first reflected echo E1 and a second signal Z2 from the second reflected echo E2.

Meanwhile, as shown on the right side of FIG. 1, in a case where there is the defect 2a inside the object to be inspected 2, when ultrasonic waves U are emitted from the ultrasonic probe 1, the first reflected echo E1 is received from the surface 2b of the object to be inspected 2, and the second reflected echo E2 is received from the back surface 2c of the object to be inspected 2, whereas a third reflected echo E3 is received from a surface of the defect 2a of the object to be inspected 2. At this step, a measurement signal S2 includes the first signal Z1 from the first reflected echo E1, the second signal Z2 from the second reflected echo E2, and a third signal Z3 from the third reflected echo E3. In this way, the defect 2a can be confirmed from the third signal Z3.

In the present invention, the ultrasonic probe 1 is used for inspecting defects inside the target material. The target material is used as a sputtering target.

Figure 2:
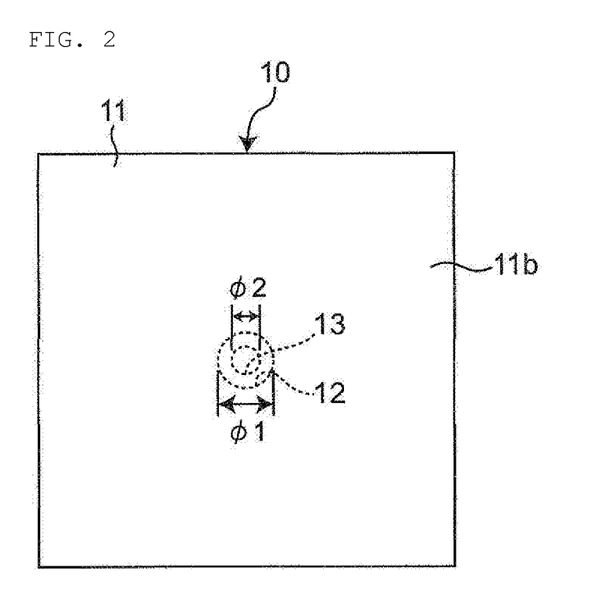
FIG. 2 It is a plan view showing a first embodiment of a pseudo defect sample of the present invention.
Figure 3:
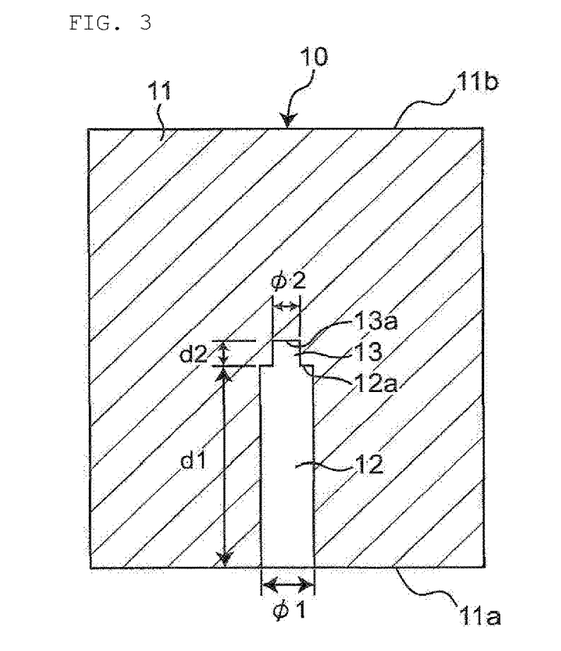
FIG. 3 It is a cross-sectional view showing the first embodiment of the pseudo defect sample of the present invention.

FIG. 2 is a plan view showing a first embodiment of a pseudo defect sample in the present invention. FIG. 3 is a cross-sectional view showing the first embodiment of the pseudo defect sample in the present invention. As shown in FIGS. 2 and 3, the pseudo defect sample 10 includes a substrate 10. The substrate 10 includes a first surface 11a and a second surface 11b opposed to the first surface 11a.

The substrate 10 has a counterbore 12 formed therein from a side of the first surface 11a to a first depth d1 and a flat-bottomed hole 13 formed in a part of a bottom surface 12a of the counterbore 12, from the bottom surface 12a of the counterbore 12 to a second depth d2. Although the relationship between the first depth d1 and the second depth d2 is not particularly limited, the first depth d1 is preferably larger than the second depth d2 when the thickness of the pseudo defect sample 10 is increased, particularly when the second depth d2 exceeds 4 mm. The counterbore 12 and the flat-bottomed hole 13 are circular, and the flat-bottomed hole 13 may be provided in a part of the bottom surface 12a of the counterbore 12, but the flat-bottomed hole 13 is disposed concentrically with the counterbore 12 as viewed from the side of the second surface 1ib, that is, the flat-bottomed hole 13 is preferably disposed at the center of the counterbore 12. By placing the flat-bottomed hole 13 concentrically with the counterbore 12, the position of the flat-bottomed hole can be easily found, especially when the diameter of the flat-bottomed hole is small. The diameter φ1 of the counterbore 12 is larger than the diameter φ2 of the flat-bottomed hole 13. Further, in general, the bottom surface of the counterbore or the flat-bottomed hole is a substantially flat surface and preferably a flat surface and is also preferably a surface substantially perpendicular to an irradiation direction of ultrasonic waves and preferably a surface perpendicular thereto in order to facilitate reflection of the ultrasonic waves emitted from the ultrasonic probe.

The ratio φ/d of an equivalent circle diameter φ of the flat-bottomed hole 13 to the second depth d of the flat-bottomed hole 13 is 0.08 or more and less than 0.40 when the equivalent circle diameter φ of the flat-bottomed hole 13 is less than 0.3 mm; 0.1 or more and less than 0.60 when the equivalent circle diameter φ of the flat-bottomed hole 13 is 0.3 mm or more and less than 0.4 mm; and 0.11 or more and less than 1.60 when the equivalent circle diameter φ of the flat-bottomed hole 13 is 0.4 mm or more. A second depth d of the flat-bottomed hole 13 refers to a second depth d2 extending from the bottom surface 12a of the counterbore 12 to a bottom surface 13a of the flat-bottomed hole 13 in the present embodiment. The reason why the ratio φ/d with respect to the depth d varies depending on the size of the equivalent circle diameter φ is that when the ratio φ/d is large (when the distance between the bottom surface 12a of the counterbore 12 and the bottom surface 13a of the flat-bottomed hole 13 is small), the reflected echo of the bottom surface 12a of the counterbore 12 becomes extremely strong and thus overlaps with the reflected echo of the bottom surface 13a of the flat-bottomed hole 13. Consequently, the reflected echo of the bottom surface 12a of the counterbore 12 cannot be separated from the echo of the bottom surface 13a of the flat-bottomed hole 13. Meanwhile, when the ratio φ/d is small (when the distance between the bottom surface 12a of the counterbore 12 and the bottom surface 13a of the flat-bottomed hole 13 is large) and in particular when φ is small, the reflected echo itself of the bottom surface 13a of the flat-bottomed hole 13 becomes weak, which makes the detection of the reflected echo difficult.

The equivalent circle diameter φ of the flat-bottomed hole 13 refers to the diameter φ2 of the circle because the flat-bottomed hole 13 is circular. When the flat-bottomed hole is not circular, the equivalent circle diameter φ of the flat-bottomed hole 13 refers to the diameter of a circle having the circular area equal to the area of the flat-bottomed hole. Specifically, assuming that S is the area of the flat-bottomed hole, the equivalent circle diameter φ is $(4S/\pi)^{1/2}$.

According to the pseudo defect sample 10, when the sensitivity adjustment of the ultrasonic flaw detection is performed in the adjustment of the ultrasonic flaw detection measurement condition using the pseudo defect sample 10, the reflected echo from the bottom surface 13a of the flat-bottomed hole 13 can be recognized even if the ultrasonic waves emitted from the ultrasonic probe are focused on the bottom surface 12a of the counterbore 12.

Figure 4:
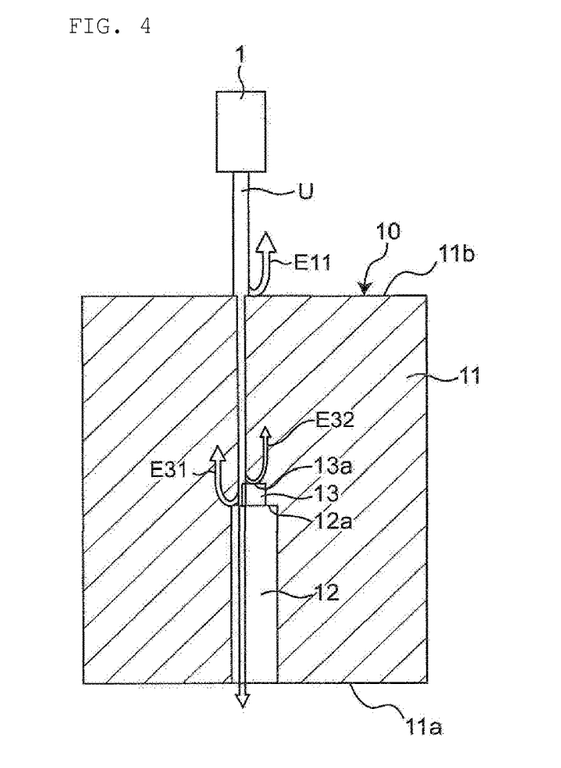
FIG. 4 It is an explanatory diagram explaining a method for adjusting an ultrasonic flaw detection measurement condition using the pseudo defect sample.

Specifically, as shown in FIG. 4, the ultrasonic probe 1 transmits the ultrasonic waves U from the second surface 11b to the first surface 11a of the substrate 11. At this step, the ultrasonic waves emitted from the ultrasonic probe are focused on the bottom surface 12a of the counterbore 12. Subsequently, the first reflected echo E11 is received from the second surface 1ib of the substrate 11, the second reflected echo E31 is received from the bottom surface 12a of the counterbore 12, and the third reflected echo E32 is received from the bottom surface 13a of the flat-bottomed hole 13.

Figure 5:
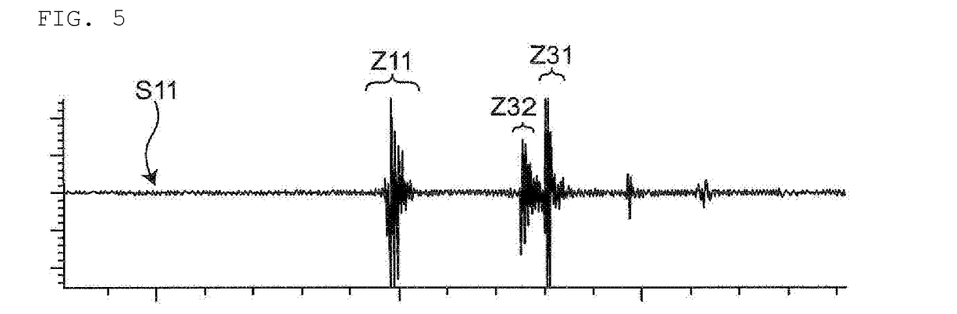
FIG. 5 It is a waveform diagram showing a measurement signal when $\phi$ is 0.2 mm and $\phi/d$ is 0.08 or more and less than 0.40.

As shown in FIG. 5, the measurement signal S11 at this step includes a first signal Z11 from the first reflected echo E11, a second signal Z31 from the second reflected echo E31, and a third signal Z32 from the third reflected echo E32. In FIG. 5, the horizontal axis represents the measurement pitch, and the vertical axis represents the intensity (gain) of the reflected echo. In this way, the third signal Z32 can be identified from the measurement signal S11, thereby making it possible to recognize the position of the bottom surface 13a of the flat-bottomed hole 13. FIG. 5 shows a case where the diameter φ2 (equivalent circle diameter φ of the flat-bottomed hole 13 is 0.2 mm.

Therefore, since the equivalent circle diameter φ of the flat-bottomed hole 13 is Less than 0.3 mm and the ratio φ/d is 0.08 or more and less than 0.40, the ultrasonic waves emitted from the ultrasonic probe can be focused on the bottom surface 12a of the larger counterbore 12 which is easy to detect, so that the smaller flat-bottomed hole 13 can be recognized in such a state. Because of this, thereafter, the ultrasonic probe 1 can be easily positioned with respect to the flat-bottomed hole 13, which can simplify a work for focusing the ultrasonic waves emitted from the ultrasonic probe on the bottom surface 13a of the flat-bottomed hole 13. Therefore, the sensitivity adjustment of the ultrasonic flaw detection becomes easy, so that the time required for the adjustment of the ultrasonic flaw detection measurement condition can be shortened.

Figure 6:
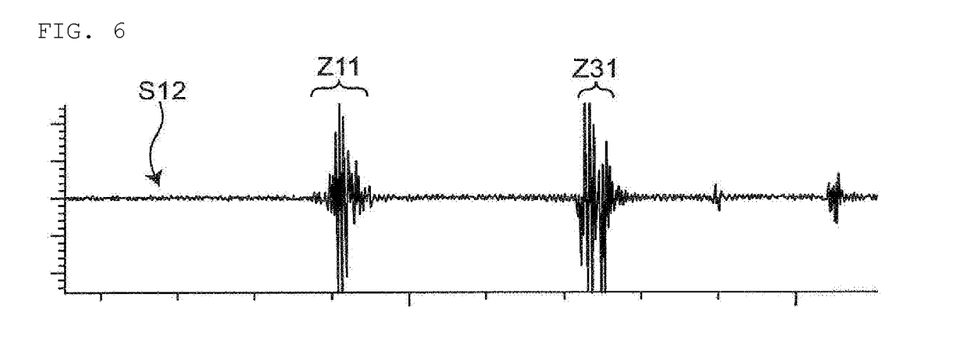
FIG. 6 It is a waveform diagram showing a measurement signal when $\phi$ is 0.2 mm and $\phi/d$ is 0.40 or more.

Meanwhile, when the ratio φ/d is 0.40 or more, as shown in FIG. 6, the measurement signal S12 at this step includes the first signal Z11 from the first reflected echo E11 (the second surface 11b of the substrate 11) and the second signal Z31 from the second reflected echo E31 (the bottom surface 12a of the counterbore 12). The third signal Z32 from the third reflected echo E32 (the bottom surface 13a of the flat-bottomed hole 13) overlaps with the second signal Z31 and thus cannot be identified from the second signal Z31. In short, if the distance from the bottom surface 12a of the counterbore 12 to the bottom surface 13a of the flat-bottomed hole 13 is not sufficiently large (d becomes small), the second reflected echo E31 from the counterbore 12 is so strong that the third reflected echo E32 from the flat-bottomed hole 13 overlaps with the second reflected echo E31 from the counterbore 12. Consequently, the third reflected echo E32 from the flat-bottomed hole 13 cannot be separated from the second reflected echo E31. Thus, the flat-bottomed hole 13 cannot be recognized.

Figure 7:
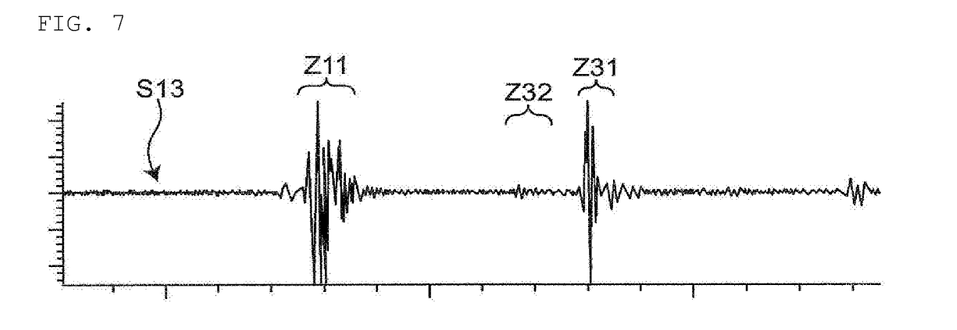
FIG. 7 It is a waveform diagram showing a measurement signal when $\phi$ is 0.2 mm and $\phi/d$ is less than 0.08.

Meanwhile, when the ratio ϕ/d is less than 0.08, as shown in FIG. 7, the measurement signal S13 at this step includes the first signal Z11 from the first reflected echo E11 (the second surface 11b of the substrate 11) and the second signal Z31 from the second reflected echo E31 (the bottom surface 12a of the counterbore 12). The third signal Z32 from the third reflected echo E32 (the bottom surface 13a of the flat-bottomed hole 13) is small and thus cannot be identified. In short, if the distance from the bottom surface 12a of the counterbore 12 to the bottom surface 13a of the flat-bottomed hole 13 is extremely long (d becomes large), the focus of the third reflected echo E32 from the flat-bottomed hole 13 is shifted, so that the third reflected echo E32 from the flat-bottomed hole 13 becomes weaker, making it difficult to search for the flat-bottomed hole 13. When the equivalent circle diameter ϕ of the flat-bottomed hole is less than 0.3 mm, the ratio ϕ/d is preferably 0.08 or more and less than 0.40, more preferably 0.08 or more and 0.3 or less, still more preferably 0.08 or more and 0.27 or less. The equivalent circle diameter ϕ of the flat-bottomed hole is normally 0.1 mm or more.

When the equivalent circle diameter ϕ of the flat-bottomed hole 13 is 0.3 mm or more and less than 0.4 mm, the ratio ϕ/d is 0.1 or more and Less than 0.60, so that the sensitivity adjustment of the ultrasonic flaw detection becomes easy in the same manner as in FIG. 5, thereby making it possible to shorten the time required for the adjustment of the ultrasonic flaw detection measurement condition. Meanwhile, if the ratio ϕ/d is 0.60 or more, like FIG. 6, the flat-bottomed hole 13 cannot be identified. In contrast, when the equivalent circle diameter ϕ of the flat-bottomed hole 13 is less than 0.3 mm, Like FIG. 7, the flat-bottomed hole 13 cannot also be identified. When the equivalent circle diameter ϕ of the flat-bottomed hole is 0.3 mm or more and less than 0.4 mm, the ratio ϕ/d is preferably 0.1 or more and less than 0.60, more preferably 0.1 or more and 0.5 or less, and still more preferably 0.1 or more and 0.4 or less.

When the equivalent circle diameter ϕ of the flat-bottomed hole 13 is 0.4 mm or more, the ratio ϕ/d is 0.11 or more and less than 1.60, so that like FIG. 5, the sensitivity adjustment of the ultrasonic flaw detection becomes easy, thereby making it possible to shorten the time required for the adjustment of the ultrasonic flaw detection measurement condition. Meanwhile, if the ratio ϕ/d is 1.60 or more, like FIG. 6, the flat-bottomed hole 13 cannot be identified. In contrast, when the equivalent circle diameter ϕ of the flat-bottomed hole 13 is less than 0.11 mm, like FIG. 7, the flat-bottomed hole 13 cannot also be identified. When the equivalent circle diameter ϕ of the flat-bottomed hole 13 is 0.4 mm or more, the ratio ϕ/d is preferably 0.11 or more and less than 1.60, more preferably from 0.11 to 1.1, and still more preferably 0.11 or more and 0.9 or less.

According to the pseudo defect sample 10, the equivalent circle diameter ϕ of the flat-bottomed hole 13 is preferably 0.5 mm or less. At this step, the flat-bottomed hole 13 is small, which makes it difficult to focus the ultrasonic waves emitted from the ultrasonic probe directly on the bottom surface 13a of the flat-bottomed hole 13. However, since the ratio ϕ/d is within the range of the above-mentioned embodiments of the present application, the ultrasonic waves emitted from the ultrasonic probe are focused on the bottom surface 12a of the counterbore 12, and thus the flat-bottomed hole 13 can be recognized. Therefore, the flat-bottomed hole 13 that would be difficult to directly recognize can be easily recognized.

The equivalent circle diameter ϕ of the flat-bottomed holes 13 is preferably 0.1 mm or more and less than 0.3 mm, and more preferably from 0.1 mm to 0.25 mm. At this step the flat-bottomed hole 13 is very small, but in the present embodiment, the flat-bottomed hole 13 can be easily recognized.

Material of the substrate 11 is not particularly limited as long as it is a material composed of a ceramic, such as metal, an alloy, an oxide, or a nitride, or a sintered body, may be composed of a conductive material and may be appropriately selected depending on the application and purpose of the substrate. Examples of such materials include aluminum, copper, titanium, silver, an alloy containing at least one of these metal elements, tin-doped indium oxide (ITO), aluminum-doped zinc oxide (AZO), gallium-doped zinc oxide (GZO), titanium-doped zinc oxide, and In—Ga—Zn-based complex oxide (IGZO). Among these, aluminum, copper, titanium, silver, or an alloy containing at least one of these metal elements is a material that tends to cause voids (defects) when the target material is produced by melt casting. Therefore, in a case where a sputtering target is produced from a target material made of any of these materials, the pseudo defect sample 10 made of such a material is preferably used to perform the ultrasonic flaw inspection. Further, the substrate 11 can be made of the same metal material as the target material, and thus the ultrasonic flaw detection measurement condition for inspecting the target material can be appropriately set.

A process for producing the pseudo defect sample 10 will be described below with reference to FIG. 3.

The counterbore 12 is formed in the substrate 11 from the side of the first surface 11a to the first depth d1. Thereafter, the flat-bottomed hole 13 is formed in a part of the bottom surface 12a of the counterbore 12 to extend from the bottom surface 12a to a second depth d2. At this step, the ratio ϕ/d of an equivalent circle diameter ϕ (diameter ϕ2 in the present embodiment) of the flat-bottomed hole 13 to the second depth d (second depth d2 in the present embodiment) of the flat-bottomed hole 13 is 0.08 or more and less than 0.40 when the equivalent circle diameter ϕ of the flat-bottomed hole 13 is less than 0.3 mm; 0.1 or more and less than 0.60 when the equivalent circle diameter ϕ of the flat-bottomed hole 13 is 0.3 mm or more and less than 0.4 mm; and 0.11 or more and less than 1.60 when the equivalent circle diameter ϕ of the flat-bottomed hole 13 is 0.4 mm or more.

The pseudo defect sample 10 is used to adjust the ultrasonic flaw detection measurement condition, thereby making the sensitivity adjustment of the ultrasonic flaw detection easy, so that the time required for the adjustment of the ultrasonic flaw detection measurement condition can be shortened. When the flat-bottomed hole 13 having a desired depth is to be provided, as the diameter of a drill is decreased, the maximum length of the drill generally becomes shorter to be about 2 to 10 mm, so that the length of the drill tends to be limited. However, in the present embodiment, by processing the counterbore 12 to a position immediately before the desired depth, the flat-bottomed hole 13 can be formed at a desired position.

A method for adjusting an ultrasonic flaw detection measurement condition using the above-mentioned pseudo defect sample 10 will be described below with reference to FIG. 4.

The ultrasonic waves U from the ultrasonic probe 1 are emitted from the second surface 1ib of the substrate 11 toward the first surface 11a, and then the ultrasonic waves emitted from the ultrasonic probe are focused on the bottom surface 12a of the counterbore 12.

Subsequently, the ultrasonic probe receives the second reflected echo E31 reflected from the bottom surface 12a of the counterbore 12 and also receives the third reflected echo E32 reflected from the bottom surface 13a of the flat-bottomed hole 13. Thereafter, the ultrasonic waves emitted from the ultrasonic probe are focused on the bottom surface 13a of the flat-bottomed hole 13 based on the third reflected echo E32, thereby adjusting the focus of the ultrasonic waves.

Even if the ultrasonic waves emitted from the ultrasonic probe are focused on the counterbore 12, the third reflected echo E32 from the bottom surface 13a of the flat-bottomed hole 13 can be recognized by being distinguished from the second reflected echo E31 from the bottom surface 12a of the counterbore 12. In this way, the ultrasonic waves emitted from the ultrasonic probe can be focused on the bottom surface 12a of the larger counterbore 12 which is easy to detect, so that the smaller flat-bottomed hole 13 can be recognized in such a state. Because of this, when the ultrasonic flaw detection measurement condition is set, the ultrasonic probe 1 can be easily positioned with respect to the flat-bottomed hole 13, which can simplify a work for focusing the ultrasonic waves emitted from the ultrasonic probe on the bottom surface 13a of the flat-bottomed hole 13. Therefore, the sensitivity adjustment of the ultrasonic flaw detection becomes easy, so that the time required for the adjustment of the ultrasonic flaw detection measurement condition can be shortened.

A method for inspecting the target material will be described below with reference to FIG. 1.

The ultrasonic probe 1 transmits the ultrasonic waves U to the target material (object to be inspected 2) while scanning under the ultrasonic flaw detection measurement condition adjusted by the above-mentioned adjustment method. Then, the reflected echoes that have been reflected from the target material are measured. Based on the measurement results, it is determined whether the target material is a good product or not. Therefore, by using the high-accuracy ultrasonic probe 1, the quality of the target material can be determined satisfactorily.

A process for producing a sputtering target will be described below.

An embodiment of the manufacturing method includes the steps of determining a defect within the target material by the above-mentioned inspection method and machining the target material substantially free of defects therein.

Machining includes cutting, milling, lathing, end milling, and the like. The target material can be produced by being finished through machining to have a desired size or surface state.

Figure 8:
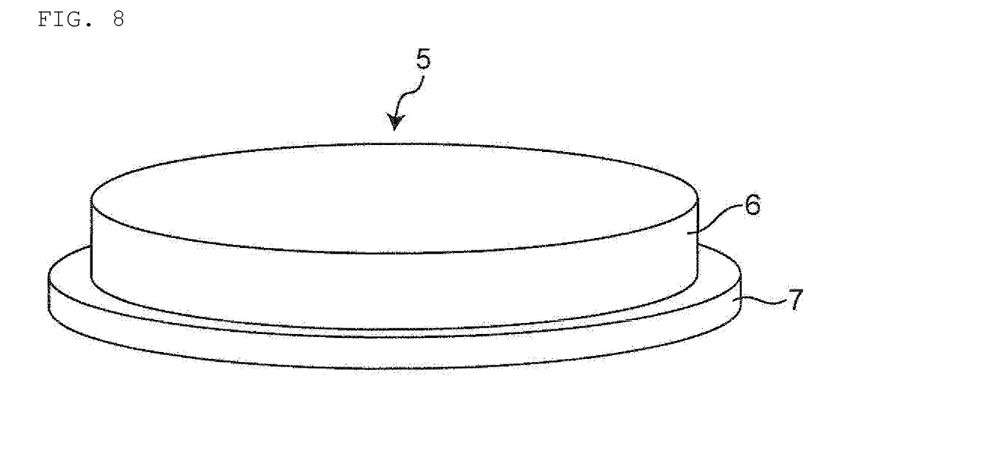
FIG. 8 It is a perspective view of a sputtering target.

In another embodiment of the above manufacturing method, defects in the target material are determined by the inspection method. Then, as shown in FIG. 8, a target material 6 that has been determined to be substantially free of defects therein is joined to a support member 7. Here, the expression "substantially free of defect" means that when the target material is inspected by the inspection method, no defect is detected, or there Ls no defect that has the size equal to or larger than that of the flat-bottomed hole. Hereinafter, a target material having substantially no defects therein is sometimes referred to as a "good product".

Although the target material 6 can be processed into a substantially plate shape, a method for processing the target material into the plate shape is not particularly limited. For example, a rectangular parallelepiped or cylindrical target material obtained by melting or casting is subjected to plastic processing such as rolling, extrusion, or forging, and then subjected to machining such as cutting, milling, lathing, or end milling, whereby the target material can be produced by being finished to a desired size or surface state.

A composition of the target material is not particularly limited as long as it is a material which can be normally used for deposition by the sputtering and is composed of a ceramic, such as metal, an alloy, an oxide, or a nitride, or a sintered body. Hence, the composition of the target material may be appropriately selected depending on the application and purpose thereof.

Examples of the target material include aluminum, copper, titanium, silver, an alloy mainly containing one of these metal elements, tin-doped indium oxide (ITO), aluminum-doped zinc oxide (AZO), gallium-doped zinc oxide (GZO), titanium-doped zinc oxide, and In—Ga—Zn-based complex oxide (IGZO). To exhibit the effects of the present invention, the target material is preferably aluminum, copper, titanium, silver or an alloy containing at least one of these elements as a main component, and more preferably aluminum with high purity.

The shape and size of the target material 6 are not particularly limited, and the target material 6 may be formed in a disk shape or a longitudinal plate shape. When the target material 6 has a disk shape, the diameter of the target material 6 is, for example, 100 mm to 700 mm, preferably 250 mm to 500 mm, and more preferably 300 mm to 450 mm. When the target material 6 has a longitudinal plate shape, the length in a short side direction of the target material 6 is, for example, 100 mm to 2000 mm, preferably 150 mm to 1500 mm, and more preferably 180 mm to 1000 mm. The length in a long side direction of the target material 6 is, for example, 100 mm to 4000 mm, preferably 1000 mm to 3500 mm, and more preferably 2200 mm to 3000 mm. It is noted that the length in the long side direction and the length in the short side direction may be the same or different.

The support member 7 is formed of, for example, pure copper, a Cu—Cr alloy, aluminum, such as an A2024 alloy and an A5052 alloy, copper, or an alloy containing any of them as a main component. A backing plate may be mainly used as the support member. When the target material 6 has the disk shape, the backing plate may be formed in the disk shape having a circular upper surface that has a diameter larger than, equal to, or slightly smaller than the upper surface of the target material 6. When the target material 6 has the longitudinal plate shape, the backing plate may be formed in the longitudinal plate shape having an upper surface that has long and short sides each of which is longer than, equal to, or slightly shorter than the corresponding side of the target material 6. When the target material 6 has the disk shape, the support member in use may be mainly configured by a ring portion for arranging the target material 6. The support member preferably has a flange portion to enable fixing of the support member to the sputtering apparatus.

The joining means is, for example, welding, such as electron beam welding, diffusion bonding, or solder bonding. Thus, the sputtering target 5 can be produced. The target material after the ultrasonic flaw inspection or the target material after joining to the support member may be machined to be finished to the desired size or surface state. The machining preferably employs a milling machine, an NC milling machine, a machining center, a lathe, an NC lathe, or the like.

Therefore, the use of the target material 6 of good quality can improve the quality of the sputtering target 5.

Second Embodiment

Figure 9:
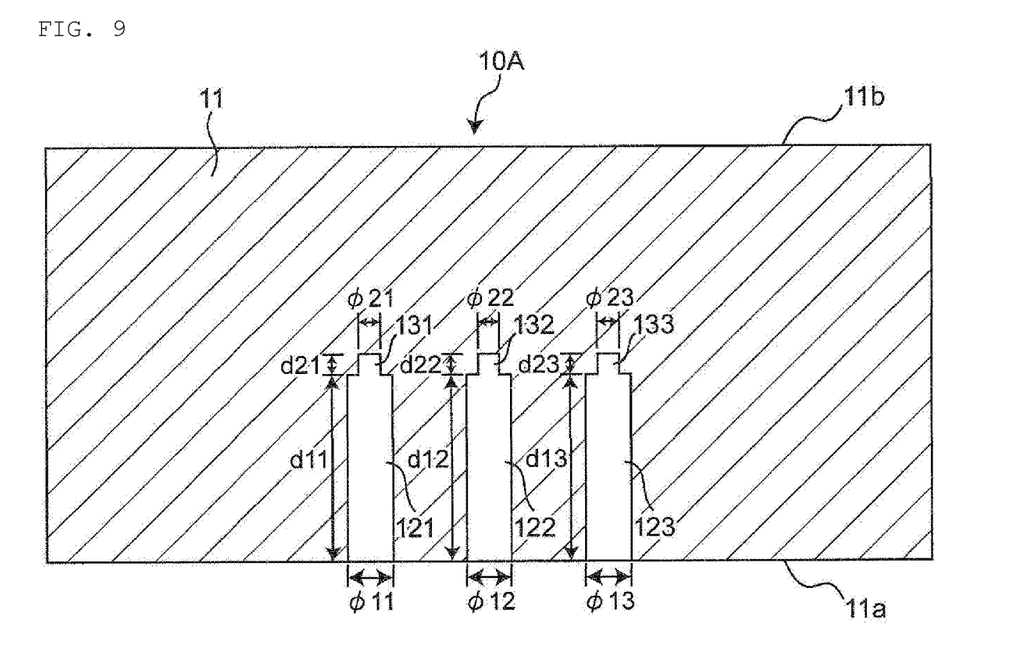
FIG. 9 It is a cross-sectional view showing a second embodiment of the pseudo defect sample of the present invention.
Figure 10:
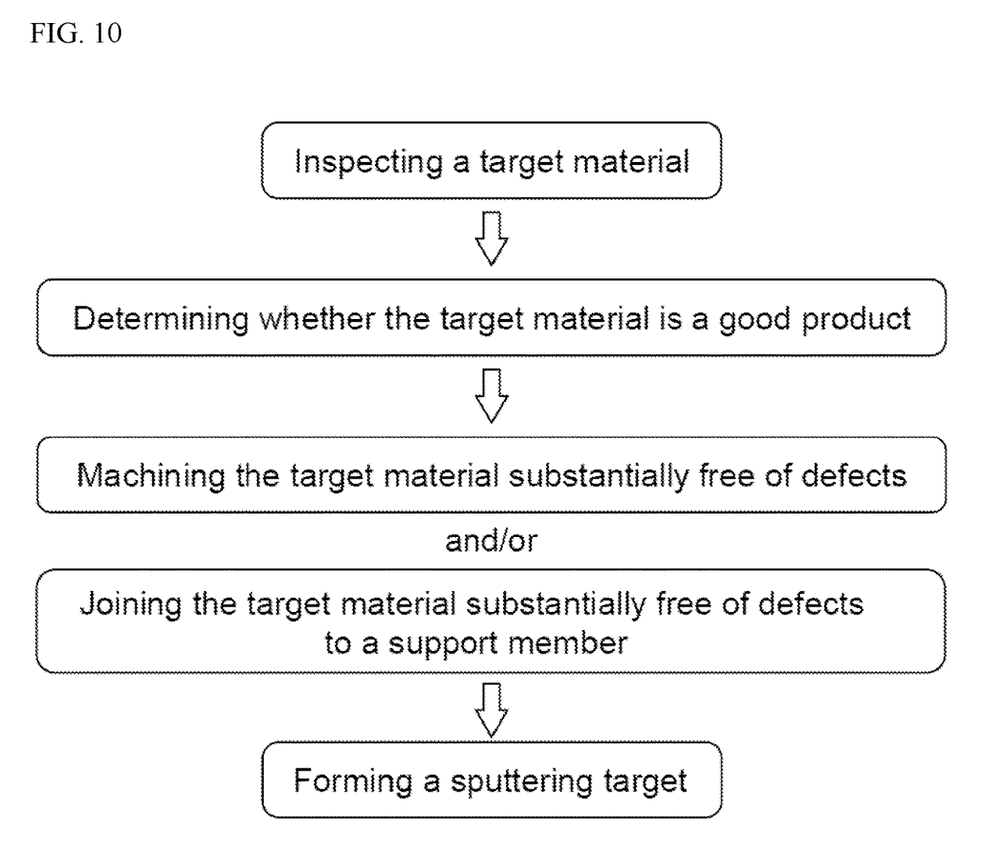
FIG. 10 It is an exemplary flowchart of processing steps for forming a sputtering target.

FIG. 9 is a cross-sectional view showing a second embodiment of the pseudo defect sample in the present invention. The second embodiment differs from the first embodiment in the number of counterbores and flat-bottomed holes. A different configuration will be described below. In the second embodiment, the same reference numerals as those in the first embodiment have the same configurations as those in the first embodiment, and thus a description thereof will be omitted.

As shown in FIG. 9, a pseudo defect sample 10A includes a plurality of sets (three sets, in the present embodiment) of counterbores 121, 122, and 123 and flat-bottomed holes 131, 132, and 133. The plurality (three in the present embodiment) of flat-bottomed holes 131, 132, and 133 has different equivalent circle diameters 4.

Specifically, these sets of the first counterbore 121 and the first flat-bottomed hole 131, the second counterbore 122 and the second flat-bottomed hole 132, and the third counterbore 123 and the third flat-bottomed hole 133 are arranged in one direction along the first surface 11a of the substrate 11.

The diameter $\phi21$ (equivalent circle diameter $\phi$) of the first flat-bottomed hole 131, the diameter $\phi22$ (equivalent circle diameter $\phi$) of the second flat-bottomed hole 132, and the diameter $\phi23$ (equivalent circle diameter $\phi$) of the third flat-bottomed hole 133 are different from each other. Each diameter $\phi21$, $\phi22$, $\phi23$ is preferably 0.5 mm or less. For example, the diameter $\phi21$ is 0.2 mm, the diameter $\phi22$ is 0.3 mm, and the diameter $\phi23$ is 0.4 mm.

In the present embodiment, the diameter $\phi11$ of the first counterbore 121, the diameter $\phi12$ of the second counterbore 122, and the diameter $\phi13$ of the third counterbore 123 are the same in FIG. 9 but may be different from each other. The first depth d11 of the first counterbore 121, the first depth d12 of the second counterbore 122, and the first depth d13 of the third counterbore 123 are the same in FIG. 9 but may be different from each other. The second depth d21 of the first flat-bottomed hole 131, the second depth d22 of the second flat-bottomed hole 132, and the second depth d23 of the third flat-bottomed hole 133 are the same in FIG. 9 but may be different from each other.

When the equivalent circle diameter $\phi$ (diameter $\phi21$) of the first flat-bottomed hole 131 is less than 0.3 mm, the ratio $\phi/d$ of the equivalent circle diameter $\phi$ of the first flat-bottomed hole 131 to the second depth d (second depth d21) of the first flat-bottomed hole 131 is 0.08 or more and less than 0.40.

When the equivalent circle diameter $\phi$ (diameter $\phi22$) of the second flat-bottomed hole 132 is 0.3 mm or more and less than 0.4 mm, the ratio $\phi/d$ of the equivalent circle diameter $\phi$ (diameter $\phi22$) of the second flat-bottomed hole 132 to the second depth d (second depth d22) of the second flat-bottomed hole 132 is 0.1 or more and less than 0.60.

When the equivalent circle diameter $\phi$ (diameter $\phi23$) of the third flat-bottomed hole 133 is 0.4 mm or more, the ratio $\phi/d$ of the equivalent circle diameter $\phi$(diameter $\phi23$) of the third flat-bottomed hole 133 to the second depth d (second depth d23) of the third flat-bottomed hole 133 is 0.11 or more and less than 1.60.

According to the pseudo defect sample 10A, in addition to exhibiting the effects of the first embodiment mentioned above, since the flat-bottomed holes having the equivalent circle diameter $\phi$ are very small, a plurality of sets of counterbores and flat-bottomed holes is provided in consideration of the processing accuracy, while the plurality of sets of the flat-bottomed holes are arranged to be located at the same distance from the second surface 11b of the pseudo defect sample 10A. Therefore, when the sensitivity of the ultrasonic flaw detection is adjusted by focusing the ultrasonic waves emitted from the ultrasonic probe, the sensitivity adjustment of the ultrasonic flaw detection can be improved by the same scanning operation. It is noted that the number of sets of counterbores and flat-bottomed holes is exemplified as three sets in FIG. 9, but may be two sets, four sets, or more. The plurality of sets of the flat-bottomed holes may have different diameters or the same diameter.

The plurality of sets of the flat-bottomed holes having respective different diameters can perform the sensitivity adjustment with higher accuracy for defects with different sizes.

The above embodiment will be described in more detail below.

(Ultrasonic Flaw Detection Measurement Method)

Ultrasonic flaw detection measurement methods include three types of measurement methods, namely, A scan, B scan, and C scan. For example, the measurement method is mentioned in the ultrasonic flaw detection imaging instrument AT-Series (Basic Edition) M671-HB-1 (Hitachi Construction Machinery Fine Tech Co., Ltd.).

The A-scan represents a temporal change of the reflected echo at a certain point and can be obtained by monitoring the voltage applied to an ultrasonic sensor with an oscilloscope or the like. This method can estimate the presence of foreign matter, a defect, or the like based on the presence or absence of reflected echo or can calculate the depth thereof by measuring a path length.

While the A scan represents the information at the certain point, the B scan develops the temporal change of the reflected echo along a certain straight line in a planar manner and represents it as planar information in the depth direction.

The C scan represents planar information of the reflected echo at a constant depth of a subject and can obtain the information by scanning the subject in the planar direction using the ultrasonic probe. This method can visualize an internal condition across the entire subject at once. In the case of detecting a fine defect distribution and a defect size over the entire target surface, the C scan method is suitable.

In the measurement method of this example, the measurement method of the C scan was used. It is noted that in the measurement method of the present invention, a measurement method of the A scan or B scan may be used.

(Focusing Method in Adjusting Ultrasonic Flaw Detection Measurement Condition)

The pseudo defect sample is put in a water tank so as to be immersed in water, and the ultrasonic probe is placed 10 to 500 mm, preferably 50 to 200 mm, and more preferably about 75 to 150 mm directly above the pseudo defect sample. At this step, the ultrasonic probe is also located in the water. The C scan is performed on the entire second surface of the pseudo defect sample to confirm the counterbore. The ultrasonic probe is moved to the confirmed counterbore, and the ultrasonic probe is placed 0.1 to 200 mm, preferably 1 to 100 mm, and more preferably about 3 to 50 mm directly above the pseudo defect sample, thereby checking the reflected echo height of the counterbore. The ultrasonic probe is operated in the vertical direction with respect to the pseudo defect sample. At this step, a position where the reflected echo height is at its maximum is searched. The position where the reflected echo height is at its maximum is the position where the counterbore comes into focus.

(Pseudo Defect Sample)

When the C scan is performed on a pseudo defect sample, the entire second surface of the pseudo defect sample needs to be scanned. Thus, it is essential that a first surface (the surface of the pseudo defect sample where the counterbore is formed) and a second surface (the surface of the pseudo defect sample irradiated with ultrasonic waves) of the pseudo defect sample have a plane substantially perpendicular to and preferably perpendicular to the irradiation direction of ultrasonic waves. The first surface and the second surface of the pseudo defect sample need to be substantially flat, and preferably flat, and the surface roughness is preferably 1.0 μm or less.

The pseudo defect sample can be perforated with a plurality of counterbores so that the plurality of counterbores can have the same depth or different depths. By perforating the pseudo defect sample with flat-bottomed holes from the counterbores, each hole corresponding to a defect size to be confirmed, the defect size to be subjected to ultrasonic flaw detection can be freely selected. Further, the depth direction in which ultrasonic flaw detection is to be performed can be freely selected depending on the depth position of the flat-bottomed hole.

In the case of performing the ultrasonic flaw detection over the entire surface in the thickness direction of the target material, it is preferable that the thickness of the pseudo defect sample is the same as the thickness of the target material, and that the position of the flat-bottomed hole is disposed at the center in the thickness direction. When the thickness of the pseudo defect sample is the same as the thickness of the target material, flaw detection of internal defects in the target can be performed immediately without modifying the measurement conditions adjusted by the pseudo defect sample.

When the position of the flat-bottomed hole in the target material is disposed at the center in the thickness direction, the sensitivity adjustment of the ultrasonic flaw detection can be performed at the center in the thickness direction, which is suitable for scanning over the entire area in the thickness direction of the target material.

The thickness of the pseudo defect sample may not be the same as the thickness of the target material, and the distance from an irradiation surface (second surface) irradiated with the ultrasonic waves to the flat-bottomed hole may be the same as the distance from the surface of the target material to the central thereof.

(Measurement in Water)

Water is used as a medium when the ultrasonic flaw detection condition is adjusted using pseudo defect samples. Some ultrasonic media vibrate and propagate acoustic waves easily or are difficult to propagate. A physical quantity representing the difficulty of propagation is called a characteristic acoustic impedance (Z) and is expressed by $Z=\rho c$ where $\rho$ is a density, c is the speed of sound, which is a value specific to the material. Water is usually used as a medium to facilitate propagation of ultrasonic waves. The water is not particularly limited as long as it does not contain a large amount of particulate impurities, dust, or the like, and, for example, tap water or pure water can be used.

As the medium other than water, a liquid such as an oil (water-soluble cutting oil, water-insoluble cutting oil, semi-dry cutting oil, motor oil, machine oil, etc.), an organic solvent (methanol, ethanol, propanol, acetone, ethylene glycol, etc.), or a gel material, such as glycerin or vaseline, is used. Water is preferably used in consideration of difficulty in obtaining, difficulty in handling, difficulty in cleaning, difficulty in maintenance, difficulty in disposal, and price.

The adjustment using the pseudo defect sample and the inspection of the target material are preferably performed in water.

(Frequency of Ultrasonic Probe in Measurement)

The frequency of the ultrasonic probe is usually measured as 5 MHz or more, but when the diameter of the flat-bottomed hole is less than 0.5 mm, the frequency of the ultrasonic probe is preferably measured at 10 MHz or more, more preferably 10 MHz or more and 50 MHz or less, still more preferably 12 MHz or more and 30 MHz or less, and particularly preferably 13 MHz or more and 20 MHz or less.

When the frequency of the ultrasonic waves is increased, the wavelength of the ultrasonic waves is shortened, so that the resolution at the time of ultrasonic flaw detection is enhanced. If the target material is aluminum (whose density is 2.7 g/cm$^3$), high-frequency ultrasonic waves are necessary. When the target material is aluminum, if the diameter of the flat-bottomed hole is less than 0.5 mm, the frequency of ultrasonic waves is preferably 10 MHz or more. If the diameter of the flat-bottomed hole is less than 0.3 mm, the frequency of ultrasonic waves is preferably 12 MHz or more.

(Counterbore)

The diameter of the counterbore needs to be larger than the diameter of the flat-bottomed hole. The diameter of the counterbore is preferably 5 mm or more because the counterbore needs to have a size enough to receive a drill in order to form a flat-bottomed hole after the counterbore is formed. When a plurality of counterbores is formed in the same pseudo defect sample, if the counterbore is extremely large, the number of holes that can be formed in the surface of the pseudo defect sample decreases or the pseudo defect sample itself becomes too large. Thus, the diameter of the counterbore is preferably 20 mm or less.

(Measurement Pitch of Ultrasonic Probe)

In order to measure fine defects, the measurement pitch of the ultrasonic waves is preferably small, but if the measurement pitch is too small, the measurement of the ultrasonic waves will take more time. Therefore, the measurement pitches are preferably 0.05 mm or more and 1.0 mm or less. The measurement pitch refers to a measurement interval when the material is scanned by the ultrasonic probe in the planar direction.

It is noted that the present invention is not limited to the above-mentioned embodiments, and design changes can be made without departing from the scope of the present invention. For example, the respective features of the first and second embodiments may be combined variously.

Examples

The relationship among the equivalent circle diameter $\phi$ of the flat-bottomed hole, the second depth d of the flat-bottomed hole, and the detection of the flat-bottomed hole was examined. In pseudo defect samples, the shape of the flat-bottomed hole was circular, and the equivalent circle diameter (diameter) $\phi$ was set to any of 0.2 mm, 0.3 mm, or 0.4 mm for each sample. The material of each of the pseudo defect samples was Al-0.5% Cu. The surface roughness on the ultrasonic irradiation side of the pseudo defect samples was set to 0.07 µm. As a measuring device, "FSLINE" (trade name) produced by Hitachi Power Solutions Co., Ltd. was used.

First, in preparation prior to measurement, an ultrasonic probe "13-1506 S-50 mm" (with a frequency of 15 MHz and a focal length of 50 mm) was attached to a measurement device.

Figure 11:
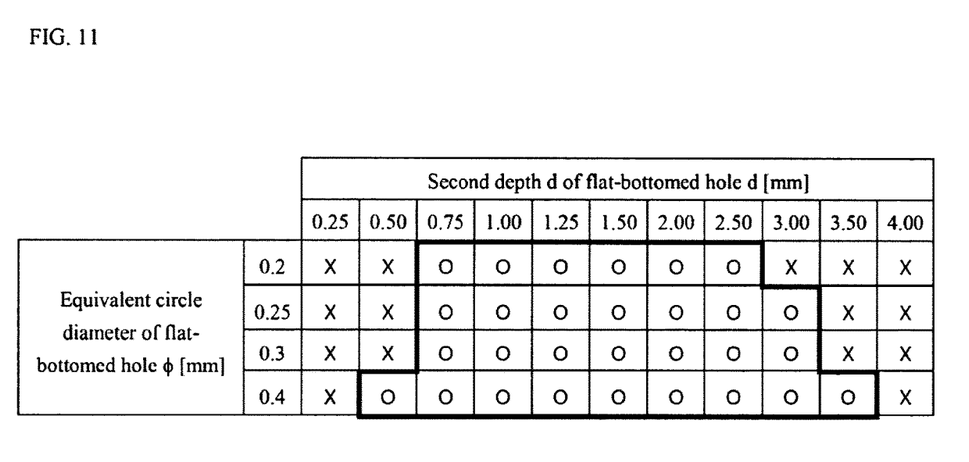
FIG. 11 It shows the examples detection data of the flat-bottomed hole when the bottom surface of the counterbore came in focus. Examples in which the flat-bottomed hole was detected as a defect were denoted by the circle sign as "O", and examples in which the flat-bottomed hole was not detected as a defect were denoted by the cross sign as "X".

Then, the pseudo defect sample was placed in a water tank of the measurement device so that the surface of the sample with the counterbore faces downward. The tank was filled with tap water. Subsequently, ultrasonic waves were irradiated from the ultrasonic probe to confirm a reflected echo from the counterbore, the ultrasonic waves were focused on the bottom surface of the counterbore, and further a reflected echo from the flat-bottomed hole was confirmed in this state. At this example, the gain was set to 22 dB. FIG. 11 shows detection data of the flat-bottomed hole when the bottom surface of the counterbore came in focus. In FIG. 11, examples in which the flat-bottomed hole was detected as a defect were denoted by the circle sign as "O", and examples in which the flat-bottomed hole was not detected as a defect were denoted by the cross sign as "X". In FIG. 11, the region denoted by the circle sign as "O" is highlighted.

As can be seen from FIG. 11, when the equivalent circle diameter $\phi$ was 0.2 mm, the flat-bottomed holes were detected if the second depth d thereof was from 0.75 mm to 2.50 mm. Meanwhile, the flat-bottomed holes were difficult to find if the second depth d thereof was 0.50 mm or less or 3.00 mm or more.

When the equivalent circle diameter $\phi$ was 0.25 mm, the flat-bottomed holes were detected if the second depth d thereof was 0.75 mm or more and 3.00 mm or less. Meanwhile, the flat-bottomed holes were difficult to find if the second depth d thereof was 0.50 mm or less or 3.50 mm or more.

When the equivalent circle diameter $\phi$ was 0.3 mm, the flat-bottomed holes were detected if the second depth d thereof was from 0.75 mm to 3.00 mm. Meanwhile, the flat-bottomed holes were difficult to find if the second depth d thereof was 0.50 mm or less or 3.50 mm or more.

When the equivalent circle diameter $\phi$ was 0.4 mm, the flat-bottomed holes were detected if the second depth d thereof was from 0.50 mm to 3.50 mm. Meanwhile, the flat-bottomed holes were difficult to find if the second depth d thereof was 0.25 mm or less or 4.00 mm or more.

Figure 12:
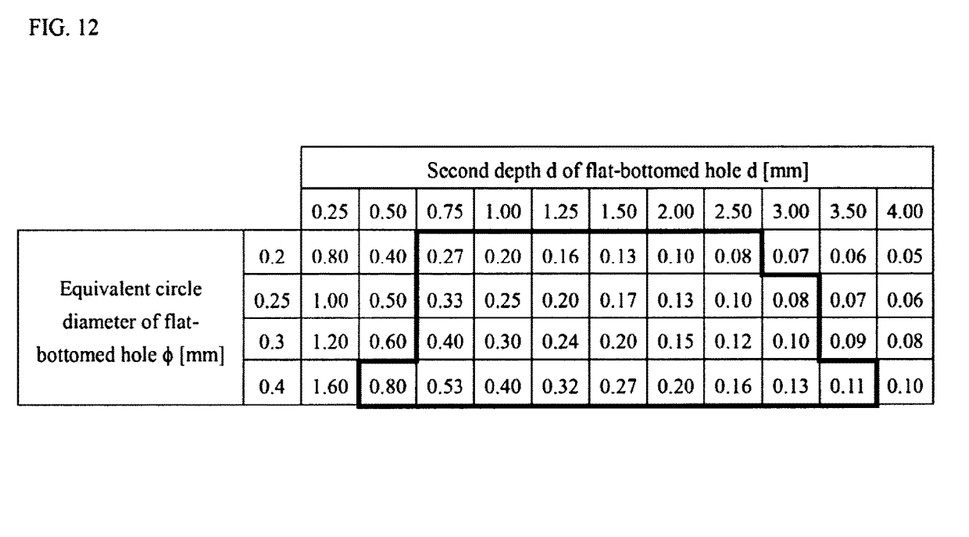

FIG. 12 shows the relationship among the equivalent circle diameter $\phi$, the second depth d, and the ratio $\phi/d$. In FIG. 12, the area of "O" denoted in FIG. 11 is highlighted.

As can be seen from FIG. 12, when the equivalent circle diameters $\phi$ of the flat-bottomed holes were 0.2 mm and 0.25 mm, respectively, the flat-bottomed holes were detected if the ratio $\phi/d$ was 0.08 or more and less than 0.40. When the equivalent circle diameter $\phi$ of the flat-bottomed hole was 0.3 mm, the flat-bottomed hole was detected if the ratio $\phi/d$ was 0.1 or more and less than 0.60. When the equivalent circle diameter $\phi$ of the flat-bottomed hole was 0.4 mm, the flat-bottomed hole was detected if the ratio $\phi/d$ was 0.11 or more and less than 1.60. It is noted that in the technique mentioned in JP 2010-145401 A, the ratio $\phi/d$ was actually measured as 0.06, so that the flat-bottomed hole was not detected. Accordingly, according to a conventional method, the ultrasonic waves emitted from the ultrasonic probe are directly focused on the flat-bottomed hole.

(Process for Producing Pseudo Defect Sample)

After cutting out a piece of 100 mm×100 mm from a plate of Al-0.5% Cu (made of the same material as the target to be subjected to ultrasonic flaw detection), a surface (surface) of the piece to be the incidence surface of the ultrasonic waves and an opposite surface (back surface) thereto were subjected to facing by a milling machine and adjusted to be one having the size of 100 mm×100 mm×t20 mm. After drilling using a portal-type machining center to form a counterbore with a diameter of $\phi$9 mm and a depth of 8 mm on the back surface, a flat-bottomed hole with a diameter of $\phi$0.2 mm and a depth of 2.0 mm (which is the depth from the counterbore, and corresponds to the depth of 10 mm from the back surface) was formed at the center of the bottom surface of the counterbore.

(Methods for Adjusting Ultrasonic Flaw Detection Measurement Condition Using Pseudo Defect Sample)

As a measuring device, "FSLINE" (trade name) manufactured by Hitachi Power Solutions Co., Ltd. was used. A pseudo defect sample was set in a water tank filled with tap water so that the surface of the sample was aligned with the upper surface of water, and an ultrasonic probe "13-1506 S-50 mm" (frequency 15 MHz, focal length 50 mm) attached to a measuring device was disposed 100 mm directly above the pseudo defect sample. At this step, the pseudo defect sample and the ultrasonic probe was present in water. Thereafter, the C scan was performed on the entire upper surface (second surface) of the pseudo defect sample to confirm the position of the counterbore. The ultrasonic probe was moved directly above the counterbore confirmed, and then the ultrasonic probe was positioned about 10 mm directly above the pseudo defect sample, thereby confirming the height of the reflected echo from the counterbore. On the condition that the ultrasonic waves were emitted from the ultrasonic probe, an ultrasonic waveform was checked on a screen of a personal computer, whereby a surface reflected echo, a back surface reflected echo, and a reflected echo of the counterbore between them were detected. In order to set the detection region of the reflected wave echo in the thickness direction, a gate was applied to include the surface reflected echo and the reflected echo of the counterbore. After confirming the reflected echo of the counterbore, the ultrasonic probe was operated and moved upward in a stepwise manner to find the position of the ultrasonic probe where the reflected echo value of the counterbore was at its maximum. When the reflected echo value of the counterbore was at its maximum, the height of the ultrasonic probe was fixed, and it was confirmed that the ultrasonic waves were focused on the bottom surface of the counterbore. At this step, the position adjustment of the ultrasonic probe in the XY direction was also performed so as to observe the reflected echo of the flat-bottomed hole based on the ultrasonic waveform.

After confirming the observation of the reflected echo of the flat-bottomed hole, the ultrasonic probe was operated and moved upward only by 2.0 mm, corresponding to the depth to the bottom surface of the flat-bottomed hole. The position of the ultrasonic probe where the reflected echo value of the flat-bottomed hole was searched. When the reflected echo value of the flat-bottomed hole was at its maximum, the height of the ultrasonic probe was fixed, and it was confirmed that the ultrasonic waves were focused on the bottom surface of the flat-bottomed hole. Since these steps made the bottom surface of the flat-bottomed hole substantially come into focus, the pseudo defect sample was subjected to the C scan under the condition of the measurement pitch of 0.1 mm and the gain of 22 dB. Here, the threshold value of a defect level was set to 96 with reference to the reflected echo intensity of the flat-bottomed hole of 0.2 mm so that a detection range of the reflected echo of the bottom surface of the flat-bottomed hole had an area of 0.03 mm² with the size of the flat-bottomed hole of ϕ0.2 mm (specifically, the settings were made in such a manner that the reflected echo intensity of 96 or more was detected as a defect, and the defect of 0.2 mm was detectable as a defect of 0.2 mm). Thereafter, the measurement conditions in which the gate was adjusted to the thickness range to be measured (the thickness of the target material to be measured) were stored in the personal computer.

(Method for Inspecting Target Material)

An Al-0.5% Cu target material having a size ϕ 460 mm×t20 mm, cut out of a rolled plate, was placed in a water tank filled with tap water so that the thickness direction of the target material was horizontal to the irradiation direction of ultrasonic waves. The measurement conditions prepared by the above-mentioned adjustment method were read out, and the range (in the XY direction) to be scanned with the ultrasonic probe was specified to be the entire upper surface of the target, whereby the ultrasonic flaw inspection was started. The measured results were compared with the threshold value of the defect level set by the above-mentioned adjustment method. It was confirmed that the defect level of 0.2 mm was not detected.

(Process for Producing Sputtering Target)

The target material that passed the ultrasonic flaw inspection was processed using an NC-lathe, and then joined to a backing plate made of A2024 alloy by diffusion-bonding according to a hot-press method. After the bonding, a finishing process was performed on the target material by the NC lathe to form a sputtering target having the size of WO mm×t18.5 mm.

DESCRIPTION OF REFERENCE NUMERALS

1 Ultrasonic probe
2 Object to be inspected
2a Defect
5 Sputtering target
6 Target material
7 Support member
10, 10A Pseudo defect sample
11 Substrate
11a First surface
11b Second surface
12 Counterbore
12a Bottom surface
13 Flat-bottomed hole
13a Bottom surface
d1 First depth
d2 Second depth
ϕ1 Diameter of counterbore (equivalent circle diameter)
ϕ2 Diameter of flat-bottomed hole (equivalent circle diameter)

The invention claimed is:

1. A pseudo defect sample for adjusting an ultrasonic flaw detection measurement to inspect a defect within a target material, the pseudo defect sample comprising a substrate which has a first surface and a second surface opposed to the first surface,
the substrate having a counterbore which is formed therein from a side of the first surface to a first depth, and a flat-bottomed hole which is formed from a bottom surface of the counterbore to a second depth and formed in a part of the bottom surface of the counterbore, and
a ratio ϕ/d of an equivalent circle diameter ϕ of the flat-bottomed hole to the second depth d of the flat-bottomed hole being:
0.08 or more and less than 0.40 when the equivalent circle diameter ϕ of the flat-bottomed hole is less than 0.3 mm;
0.1 or more and less than 0.60 when the equivalent circle diameter ϕ of the flat-bottomed hole is 0.3 mm or more and less than 0.4 mm; and
0.11 or more and less than 1.60 when the equivalent circle diameter ϕ of the flat-bottomed hole is 0.4 mm or more.

2. The pseudo defect sample according to claim 1, wherein the equivalent circle diameter ϕ of the flat-bottomed hole is 0.5 mm or less.

3. The pseudo defect sample according to claim 2, wherein the equivalent circle diameter ϕ of the flat-bottomed hole is 0.1 mm or more, and less than 0.3 mm.

4. The pseudo defect sample according to claim 1, comprising a plurality of sets of the counterbores and the flat-bottomed holes.

5. The pseudo defect sample according to claim 1, wherein the substrate is formed of aluminum, copper, titanium, silver, or an alloy containing at least one of these metal elements.

6. The pseudo defect sample according to claim 1, wherein the ultrasonic flaw detection measurement comprises performing ultrasonic flaw detection measurement with ultrasonic waves having a frequency of 5 MHz or more.

7. A process for producing a pseudo defect sample for adjusting an ultrasonic flaw detection measurement to inspect a defect within a target material,
the method comprising the steps of:
forming a counterbore from a side of a first surface to a first depth, in a substrate which has the first surface and a second surface opposed to the first surface; and
forming a flat-bottomed hole from the bottom surface to a second depth, in a part of a bottom surface of the counterbore,
a ratio ϕ/d of an equivalent circle diameter ϕ of the flat-bottomed hole to the second depth d of the flat-bottomed hole being:
0.08 or more and less than 0.40 when the equivalent circle diameter ϕ of the flat-bottomed hole is less than 0.3 mm;
0.1 or more and less than 0.60 when the equivalent circle diameter ϕ of the flat-bottomed hole is 0.3 mm or more and less than 0.4 mm; and
0.11 or more and less than 1.60 when the equivalent circle diameter ϕ of the flat-bottomed hole is 0.4 mm or more.

8. The process for producing a pseudo defect sample according to claim 7, wherein the substrate is formed of aluminum, copper, titanium, silver, or an alloy containing at least one of these metal elements.

9. A method for adjusting ultrasonic flaw detection,
the method using a pseudo defect sample according to claim 1, the method comprising the steps of:
transmitting ultrasonic waves from an ultrasonic probe in such a manner that the waves move from the second surface of the substrate of the pseudo defect sample to the first surface of the substrate, followed by confirming a reflected echo of the counterbore in the pseudo defect sample;
focusing the ultrasonic waves on the bottom surface of the counterbore based on the reflected echo of the counterbore;
receiving a reflected echo that is reflected from the bottom surface of the flat-bottomed hole in the pseudo defect sample, while receiving the reflected echo that is reflected from the bottom surface of the counterbore; and focusing the ultrasonic waves on the bottom surface of the flat-bottomed hole based on the reflected echo from the flat-bottomed hole.

10. The method for adjusting ultrasonic flaw detection measurement according to claim 9, wherein the ultrasonic flaw detection measurement comprises measurement with ultrasonic waves having a frequency of 5 MHz or more.

11. A method for inspecting a target material, the method comprising the steps of:

transmitting ultrasonic waves to a target material while, under the ultrasonic flaw detection measurement condition adjusted by the adjustment method according to claim 9, scanning the target material by using an ultrasonic probe;

measuring a reflected echo that is reflected from the target material; and determining whether the target material is a quality product or not based on a result of the measurement of defects if any therein.

12. A process for producing a sputtering target, comprising the steps of:

determining whether the target material is a quality product or not by the inspection method according to claim 11; and machining the target material that is determined as a quality product.

13. A process for producing a sputtering target, the method comprising the steps of:

determining whether the target material is a quality product or not by the inspection method according to claim 11; and joining the target material that is determined as a quality product, to a support member.

* * * * *